US008610445B2

(12) United States Patent
Diekhans et al.

(10) Patent No.: US 8,610,445 B2
(45) Date of Patent: Dec. 17, 2013

(54) AGRICULTURAL WORKING MACHINE FOR MEASURING COMPONENTS OF A CROP MATERIAL

(75) Inventors: Norbert Diekhans, Guetersloh (DE); Bastian Kriebel, Muenster (DE); Frank Claussen, Harsewinkel (DE)

(73) Assignee: CLAAS Selbstfahrende Erntemaschinen GmbH, Harsewinkel (DE)

( * ) Notice: Subject to any disclaimer, the term of this patent is extended or adjusted under 35 U.S.C. 154(b) by 683 days.

(21) Appl. No.: 12/265,427

(22) Filed: Nov. 5, 2008

(65) Prior Publication Data
US 2009/0120202 A1   May 14, 2009

(30) Foreign Application Priority Data
Nov. 9, 2007   (DE) .......................... 10 2007 053 910

(51) Int. Cl.
*G01R 27/08*   (2006.01)
*A01D 75/18*   (2006.01)

(52) U.S. Cl.
USPC ............................................. 324/694; 460/1

(58) Field of Classification Search
USPC .............................................. 324/694; 460/1
See application file for complete search history.

(56) References Cited

U.S. PATENT DOCUMENTS

| 3,491,595 | A | * | 1/1970 | Griffeth | 374/142 |
|---|---|---|---|---|---|
| 5,400,818 | A | * | 3/1995 | Cosentino et al. | 137/551 |
| 5,430,384 | A | * | 7/1995 | Hocker | 324/694 |
| 5,483,164 | A | * | 1/1996 | Moss et al. | 324/425 |
| 5,859,536 | A | * | 1/1999 | Stockton | 324/664 |
| 6,257,072 | B1 | | 7/2001 | Diekhans | |
| 6,553,813 | B2 | * | 4/2003 | Rynhart et al. | 73/73 |
| 6,789,474 | B2 | * | 9/2004 | Wang | 101/147 |
| 7,443,175 | B2 | * | 10/2008 | Podhajsky et al. | 324/663 |
| 7,679,377 | B2 | * | 3/2010 | Schroder | 324/664 |
| 2005/0178100 | A1 | * | 8/2005 | Deppe | 56/11.9 |
| 2008/0258742 | A1 | * | 10/2008 | Dimitrakopoulos et al. | 324/693 |

FOREIGN PATENT DOCUMENTS

| EP | 0 843 959 | 5/1998 |
|---|---|---|
| EP | 0 931 446 | 7/1999 |

\* cited by examiner

*Primary Examiner* — Jeff Natalini
(74) *Attorney, Agent, or Firm* — Michael J. Striker

(57) ABSTRACT

A measuring device for measuring components of a crop material is installed on an agricultural machine and includes at least one conductance sensor, determining the component "moisture content", which is determined via the temperature-compensated detection of conductance. In this manner it is ensured that the measuring device delivers reliable measurement results for determining the components of a crop material even under fluctuating measuring conditions.

15 Claims, 3 Drawing Sheets

AGRICULTURAL WORKING MACHINE FOR MEASURING COMPONENTS OF A CROP MATERIAL

CROSS-REFERENCE TO A RELATED APPLICATION

The invention described and claimed hereinbelow is also described in German Patent Application DE 10 2007 053 910.1 filed on Nov. 9, 2007. This German Patent Application, whose subject matter is incorporated here by reference, provides the basis for a claim of priority of invention under 35 U.S.C. 119(a)-(d).

BACKGROUND OF THE INVENTION

The present invention relates to a measuring device for measuring components of a crop material.

Publication EP 0 843 959 makes known an agricultural working machine designed as a forage harvester, which includes a measuring device in its upper discharge chute for detecting parameters of a crop-material flow passing through the forage harvester. The measuring device detects the crop-material properties using a microwave sensor. Special algorithms are provided that eliminate influencing quantities that may occur, or at least reduce their effect on the crop-material parameters to be detected. Due to the enormous amount of information contained in the change—caused by material flow—in the electrical field of the microwaves, it is possible—using suitable analytical software—to detect, e.g., the moisture content of the crop material flowing through the agricultural working machine. In one variant of the embodiment, it is also provided—in order to reduce possible sources of error—to also take the temperature value of the crop material into account in the analysis of the microwave signals, the temperature value being registered using separate temperature sensors.

Even though systems of this type are capable—when suitable analytical software is used—of determining a large number of crop-material parameters, microwave sensors have the disadvantage in particular that integrating them in agricultural working machines is very cost-intensive, which makes them unsuitable for widespread agricultural use, e.g., in drawn agricultural working machines. This is due, in particular, to the fact that a large number of technological conditions must be created so that the microwave signals may detect a crop-material flow with minimal interference and so that machine or crop-material-related interferences may be largely compensated for.

For this reason, e.g., a sensor system is disclosed in EP 0 931 446 that ascertains—using two electrodes—the conductance of a crop-material flow that passes by the sensor and ultimately uses the conductance that was ascertained to derive a value for the moisture content. The conductance sensor itself is composed of a peg-shaped electrode and a circular electrode, and it may be located at any point in the upper discharge chute—through which the crop material flows—of a self-propelled forage harvester. The position of the conductance sensor in the agricultural working machine is selected such that the sensor device delivers reliable measured results and is protected from wear to the greatest extent possible. A system of this type has the advantage in particular that a sensing device for parameters of a material flow passing through an agricultural working machine is created with little technical outlay and, therefore, minimal costs.

A significant disadvantage of designs of this type, however, is that an optimal position of a measuring device of this type is determined mainly by the moving behavior of the crop material in the agricultural working machine, and it may change considerably depending on the type of crop, the kinematic parameters of the various working devices, and the moisture content of the crop material. This means that it is not entirely possible to assume what a universally-valid, optimal position of the material-detection device is. As a result, the crop-material parameters detected with a device of this type does not deliver reliable measurement results in every case. Given that the moisture content has a significant influence on the determination of the throughout of crop material passing through an agricultural machine, it is very significant that the detection of the crop-material moisture detected using measurement technology deliver precise values during the working operation of the agricultural machine.

SUMMARY OF THE INVENTION

The object of the present invention, therefore, is to avoid the disadvantages of the related art and, in particular, to provide a measuring device for determining the components of a crop material that delivers reliable measured results even under fluctuating measuring conditions.

In keeping with these objects and with others, which will become apparent hereinafter, one feature of the present invention, resides, briefly stated in a measuring device for measuring components of a crop material, installable on an agricultural machine, comprising at least one conductance sensor, said at least one conductance sensor being configured for determining a component "moisture content", with the moisture content being determined via a temperature-compensated detection of conductance.

Given that the measuring device for measuring the components of a crop material in an agricultural machine includes at least one conductance sensor that determines the component "moisture content" based on a temperature-compensated detection of the conductance, it is ensured that the measuring device for determining the components of a crop material deliver reliable measured results even under fluctuating measurement conditions.

In an advantageous embodiment of the present invention, a temperature sensor is provided for temperature compensation, which may also be integrated in the conductance sensor. This has the advantage, e.g., that a well-proven technology for measuring temperature is used and that an integrated conductance-temperature sensor is created that may be installed in the particular agricultural machine in a space-saving manner.

A further improvement of the accuracy of the moisture content to be determined using the conductance sensor is attained when at least one further crop material-specific and/or machine-specific parameter is taken into account in the determination of the moisture content of the component.

In an advantageous refinement of the present invention, the at least one further crop-material specific parameter and/or machine-specific parameter is the crop-material throughput and/or the layer thickness of the crop-material flow detected by the conductance sensor and/or the crop-material type and/or the density of the crop material in the region of the conductance sensor and/or the pressing force of the crop material in the region of the conductance sensor. These parameters are of great significance because investigations have shown that conductance LW generated by the conductance sensor described is influenced mainly by the crop-material throughput moving past the conductance sensor at any moment, and by the layer thickness and material density of this crop material, since it is precisely these parameters that primarily define the conductance of the crop-material flow to be detected. Since the cellular structure of the plants that constitute the crop-material flow also influences its conductance, and this cellular structure fluctuates greatly from plant type to plant type, it is advantageous to also account for the type of crop material in the determination of the conductance.

Given that a conductance sensor generates the conductance via more or less intensive contact of its electrodes with the crop-material flow to be detected, the intensity of the contact between the crop-material flow and the electrodes is also of great significance. The conductivity of a substance that is detected decreases as the contact with a conductance sensor decreases. It is therefore also advantageous to account for the pressing force that the crop-material flow exerts on the electrodes, since the pressing force is ultimately synonymous with the intensity of the contact between the crop-material flow to be detected and the conductance sensor.

In a further advantageous embodiment of the present invention, the agricultural working machine is designed as a forage harvester, and the crop-material specific parameter "pressing force" of the crop material is determined based on the ejection speed of the crop material in the region of the conductance sensor, the width of the passage of a post-accelerator located upstream of the conductance sensor, and/or the impact point of the crop-material flow in the region of the conductance sensor, since it is precisely this parameter that describes the intensity with which the crop-material flow is pressed against the conductance sensor.

In a further advantageous embodiment of the present invention, the at least one conductance sensor includes three electrodes, the electrodes being positioned in a triangular configuration, so that, when a single electrode is acted upon with an electrical current, a conductance may be determined at the other two electrodes, thereby making it possible to compare the conductances and use the more suitable conductance to determine the moisture content.

Given that the triangular configuration of the electrodes of the conductance sensor is oriented in or against the direction of material flow, it is also ensured that the conductance sensor may be operated in two different installation positions, so that, when wear typically occurs on one side, the conductance sensor may be rotated, so that the side of the conductance sensor that previously pointed downstream now points upstream into the crop-material flow. The service life of the conductance sensor is thereby increased, which ultimately decreases the maintenance effort and expense.

A compact, space-saving, and more cost-favorable design of the inventive measuring device also results given that the temperature sensor is assigned to at least one of the electrodes of the conductance sensor.

Provided that the agricultural working machine is designed as a forage harvester, the conductance sensor may be positioned on the inside of an upper discharge chute that ejects the crop-material flow, and in the region of impact of the crop-material flow that is accelerated by the post-accelerator. This has the advantage in particular that intensive contact between the crop-material flow and the conductance sensor is always ensured.

To ensure that two conductances may be determined using the three electrodes assigned to the conductance sensor and that the suitable conductance may be selected, the electrodes of the conductance sensor are coupled with each other such that a conductance bridge may always be formed between two electrodes, and a comparison of the detected conductances and the selection of the more suitable conductance may be carried out using a control and evaluation unit.

A structure with a simpler design that determines only one conductance results in an advantageous embodiment of the present invention when at least two electrodes of the conductance sensor are short-circuited, so that only one conductance measurement bridge results between the electrodes, and the determined conductance value LW is transmitted to an evaluation unit (29, 38).

To compensate for the measurement error that occurs due to electrode wear, it may be provided in a further advantageous embodiment of the present invention for the vertical positioning of the electrodes in the conductance sensor to be adjustable.

The operation of the conductance sensor in two opposite installation positions that is particularly easy to implement in terms of design is attained when the electrodes of the conductance sensor are integrated in a base plate that may be integrated in the agricultural machine in two positions that are offset by 180°.

In a further advantageous embodiment of the present invention, the wear of the electrodes may also be counteracted by covering the electrodes of the conductance sensor with enclosures made of wear-resistance material, and by designing the enclosures to be aerodynamic in the direction of material flow.

In a further advantageous embodiment of the present invention, an extremely compact design of the conductance sensor is attained when the conductance sensor includes a housing designed as a dust cover, and the signal-processing device of the conductance sensor and the evaluation unit (38) assigned to the agricultural machine are integrated in the housing designed as a dust cover, thereby enabling the conductance sensor itself to determine the moisture content in addition to the conductance.

In a further advantageous embodiment of the present invention, the components that are determined are the moisture content or its equivalent, the content of dry mass, and the moisture content and/or content of dry mass that is determined is depicted in a display unit and is stored in the evaluation unit such that it may be recalled. This has the advantage, in particular, that the component detected is shown immediately to the operator of the agricultural machine, and the value that is determined is also made available to further control and regulating processes in the agricultural machine, e.g., to determine the crop-material throughput.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
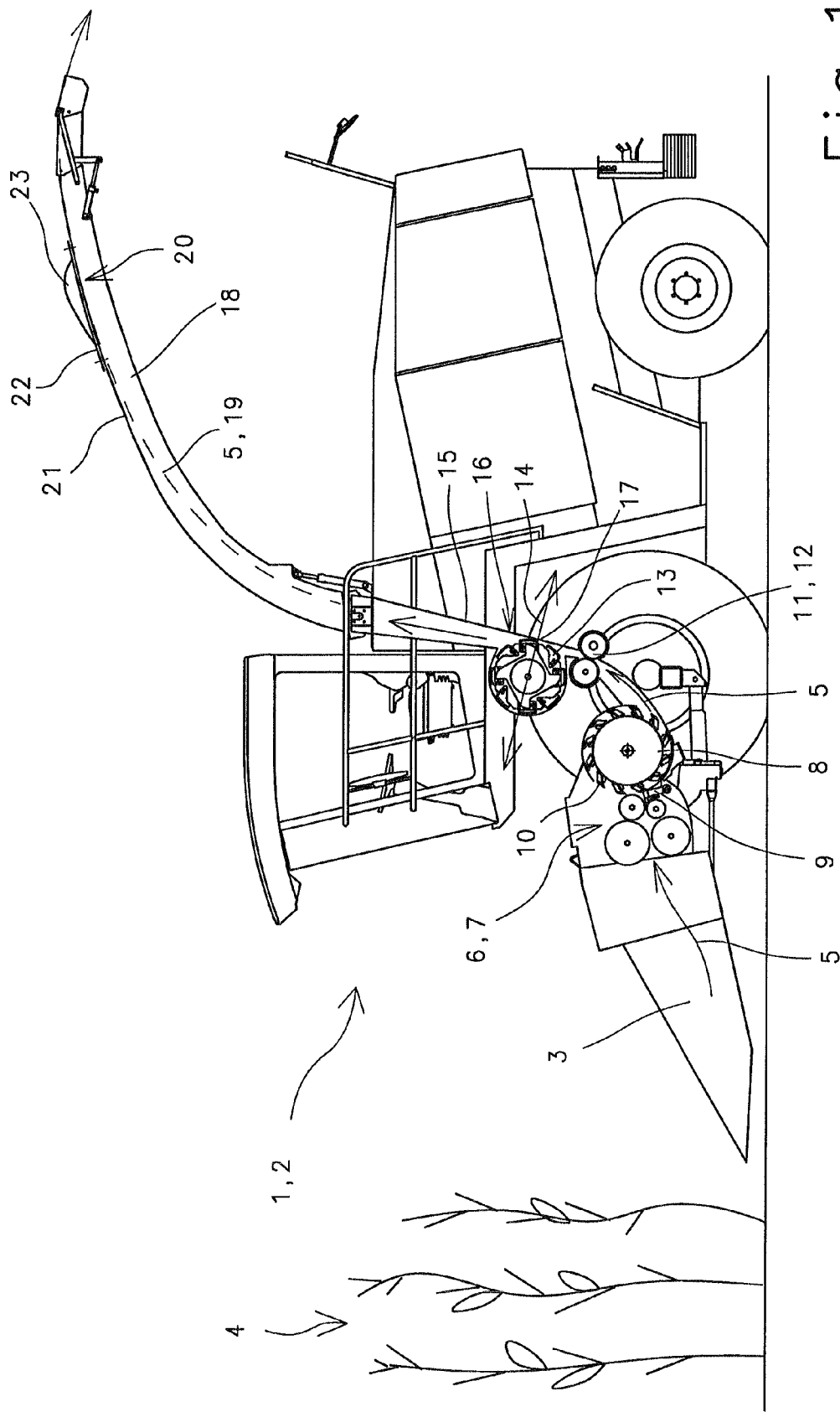
FIG. 1 shows an agricultural machine designed as a forage harvester, with an inventive measuring device

FIG. 1 shows an agricultural machine 1 designed as a forage harvester 2. Forage harvester 2 typically includes a front attachment 3 for harvesting and picking up a crop material 4 that is either standing or has already been laid down in swaths. In the rear region of front attachment 3, crop-material flow 5 ultimately reaches a precompression device 7 that is composed of intake and compression rollers 6, and that transfers crop-material flow 5 to downstream chopping unit 8. Crop-material flow 5 is cut up between shear bar 9 and rotating chopping blades and, in the rear region of chopper drum 8, is transferred to a post-fragmentation device 11, a "corn cracker" 12, depending on the type of crop material it is. Due to various rubbing effects, and due to the post-fragmentation, the kinetic energy of crop-material flow 5 gradually decreases, which is typically compensated for by a post-accelerator 13 that is located in the rear region of corn cracker 12. In the exemplary embodiment shown, the position of post-accelerator 13 may be changed according to arrow direction 14 within upper discharge chute 15, which encloses it. This change in position results in a change in the width of passage 17 that results between post-accelerator 13 and wall 16 of upper discharge chute 15. The smaller the width of passage 17, the more intensively crop-material flow 5 passing through passage 17 is accelerated. Trajectory 19 of crop-material flow 5 in upper discharge chute 18 therefore depends mainly on the acceleration effect of post-accelerator 13. In impact region 20 of material flow 5 exiting post-accelerator 13 against wall 21 of upper discharge chute 18, wall 21 is defined by a replaceable wearing plate 22, to which inventive measuring device 23 is assigned. Measuring device 23 is used to determine the components of crop-material flow 5 passing through agricultural machine 1 and will be described in greater detail below.

Figure 2:
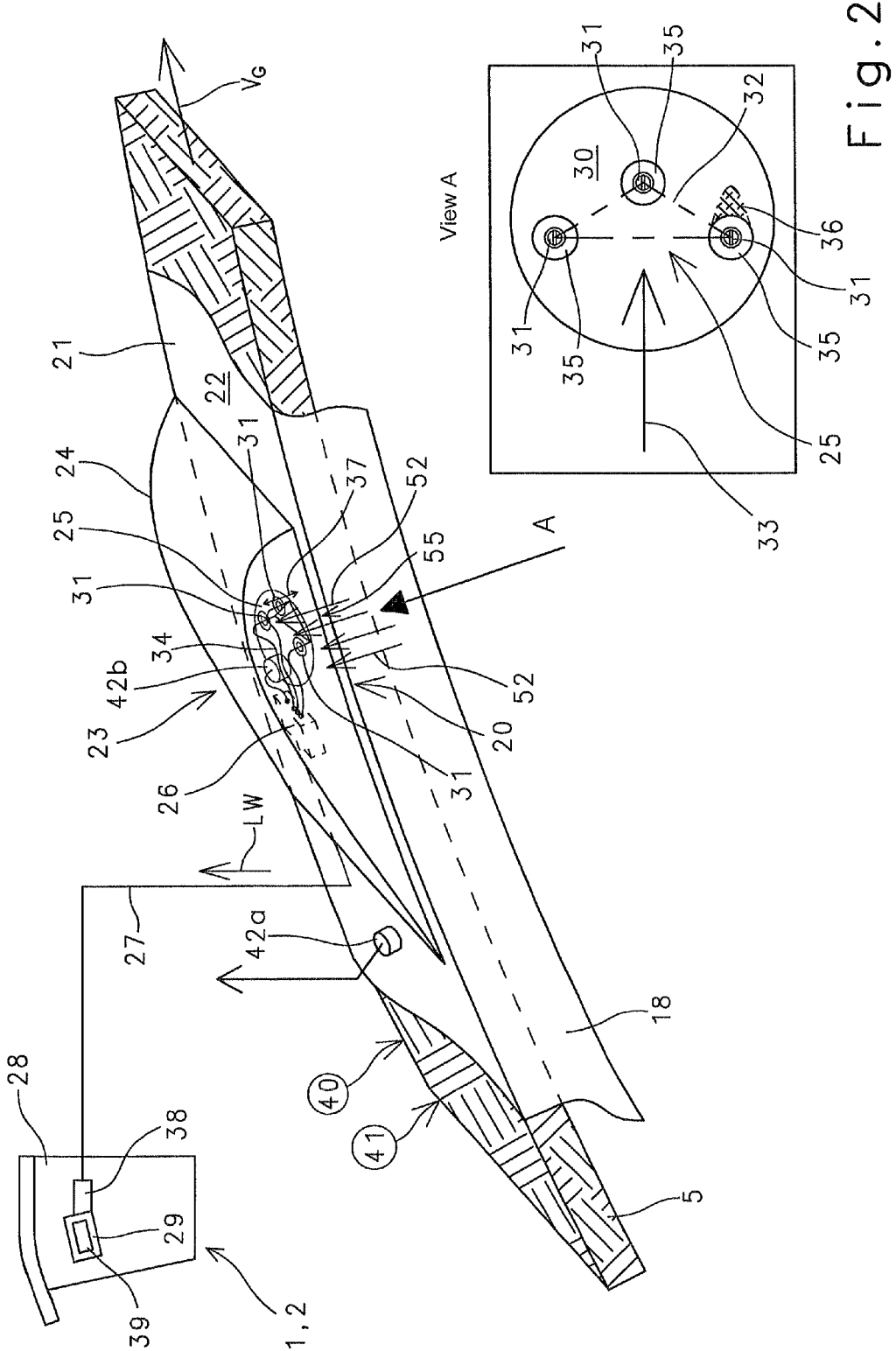
FIG. 2 shows a detailed view of the inventive measuring device

FIG. 2 shows a sectional view of upper discharge chute 18 with inventive measuring device 23. Measuring device 23 includes a dust cover 24—which is assigned to wearing plate 22 of upper discharge chute 18 on the top and outer sides—for protecting inventive conductance sensor 25 and signal-processing device 26 located therein from harmful environmental influences, e.g., moisture, dirt, and collisions with obstacles. Signal and data transmission line 27 is also guided through dust cover 24, and it is operatively connected with an evaluation and display unit 29 located in vehicle cab 28. The positioning of measuring device 23 on wearing plate 22 is selected such that it is located directly in impact region 20 of crop-material flow 5 on top wall 21 of upper discharge chute 18. According viewing direction A shown in FIG. 2, inventive conductance sensor 25—which will be described in greater detail below—is installed in wearing plate 22 on the inside. In the exemplary embodiment shown, conductance sensor 25 includes a base plate 30, through which three electrodes 31 pass. Electrodes 31 are located in a triangular configuration 32.

One of the electrodes 31 is located ahead of the other electrodes 31 in conveyance direction 33 of crop material in base plate 30 of conductance sensor 25. In signal-processing device 26, the three electrodes 31 are interconnected via lines 34 such that, whenever a current is applied to any electrode 31, the resultant conductance between this electrode and further electrodes 31 may be determined, thereby making it possible to always determine two conductances in one conductance measurement. In a simplified embodiment, it is also possible to short-circuit two of the three electrodes 31, preferably electrodes 31 that lie on a line that is transverse to material flow 33, thereby enabling conductance sensor 25 to always determine only one conductance LW. Since the distance between conductance sensor 25 and crop-material flow 5 must be as small as possible in order to realize a reliable conductance determination in a crop-material flow 5, but this may result in a great deal of wear on conductance sensor 25, electrodes 31 in contact with crop-material flow 5 are enclosed in enclosures 35 made of a wear-resistant material, preferably hard metal.

To minimize the influence of material wear, it is also feasible to enclose electrodes 31 in aerodynamic enclosures 36 that point in material-flow direction 33 and are composed of wear-resistant material, thereby resulting in a longer service life of electrodes 31. In addition, due to the triangular configuration 32 of electrodes 31 relative to each other, conductance sensor 25 may be installed on the inside of wearing plate 22 such that it is rotated by 180°, thereby also increasing the service life of conductance sensor 25 by ensuring that wear takes place evenly on both sides. For the latter case, base plate 30 must be screwed into the inside of wearing plate 22, rotated by 180°. One electrode 31 is then located downstream of the other electrodes 31 in material-flow direction 33. It is also feasible—in the simplest case—to install electrodes 31 in wearing plate 30 using screw-type connections such that they are displaceable in their axial position indicated by arrow direction 37. When wear occurs, it is therefore possible to move particular electrode 31 in the direction of crop-material flow 5 that passes by it.

It is within the framework of the present invention to locate inventive measuring device 23 at any point in an agricultural machine 1 in the direct vicinity of a crop-material flow 5 that is passing through, will pass through, or has passed through agricultural machine 1. The present invention is therefore not limited to installing measuring device 23 on a wearing plate 22 of a forage harvester 2. It is also within the framework of the present invention to locate compact evaluation and display unit 29—which is located in vehicle cab 28 of forage harvester 2 in the exemplary embodiment shown—at any point in an agricultural machine 1, and to design it as a separate evaluation unit 38 and a separate display unit 39.

In order to determine moisture content 40 of crop-material flow 5 according to the present invention and with consideration for temperature 41 of crop-material flow 5 and/or its surroundings in a temperature-compensated manner, a temperature sensor 42a, which is known per se, is also assigned to wall 21 located in impact region 20 or wearing plate 22 of upper discharge chute 18. For simplicity, the temperature sensor as indicated with reference numeral 42b may also be integrated directly in conductance sensor 25 or in one of its electrodes 31, preferably in center electrode 31. In the latter case, temperature 41 that is measured may be transferred directly via signal and data processing device 27 of inventive measuring device 23 to evaluation unit 29, 38. In the other case, a separate, not-shown data transmission line would be provided.

Figure 3:
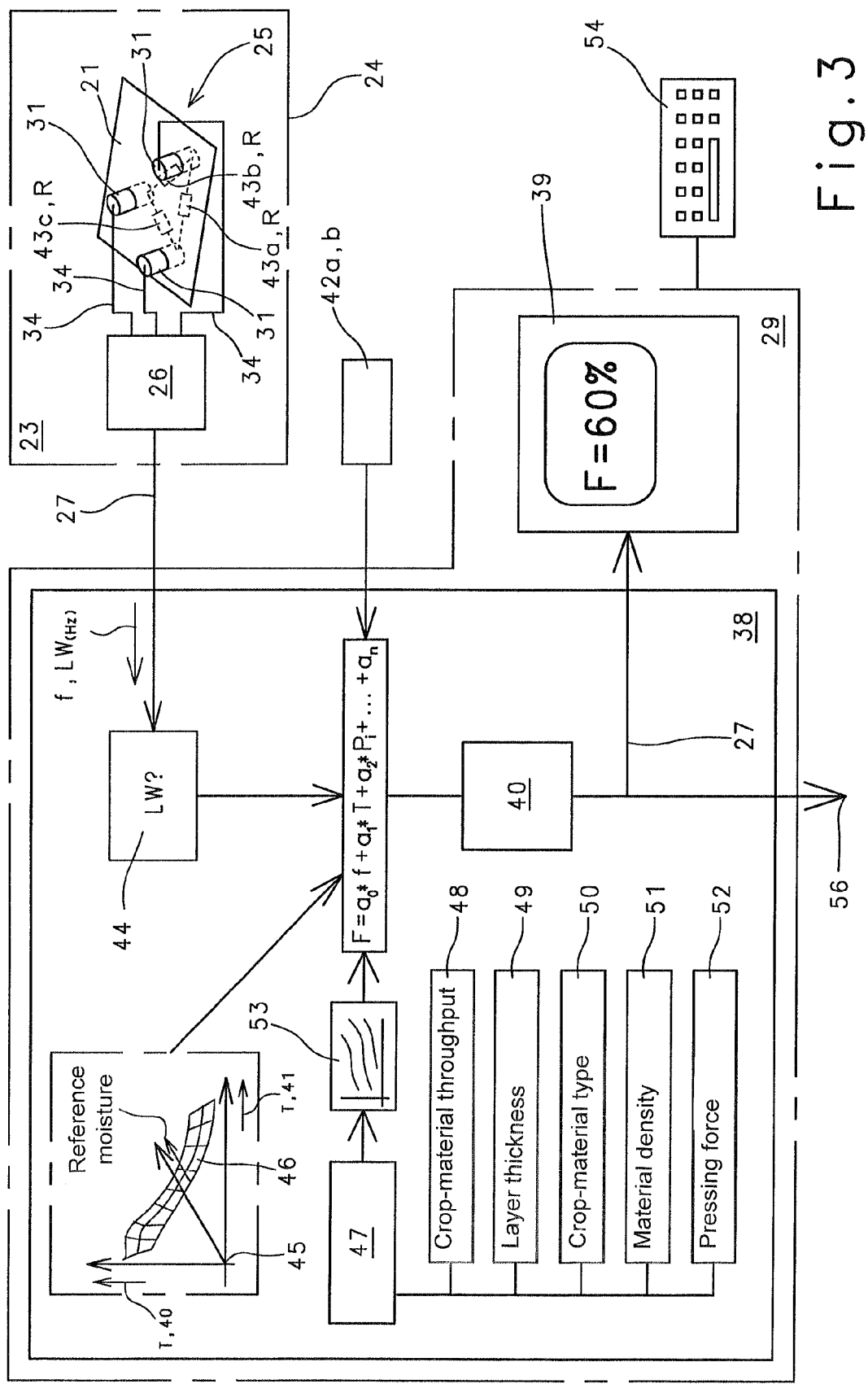
FIG. 3 shows a schematic illustration of the inventive generation of moisture content

FIG. 3 shows the details of inventive measuring device 23 for describing the essential aspects of the present invention. As mentioned above, adjacent electrodes 31 are connected with signal-processing device 26 via electrical lines 34. Conductance sensor 25 therefore includes a total of three "conductance bridges" 43, which are depicted schematically in FIG. 3 as electrical resistors R of crop-material flow 5. If two of the electrodes were short-circuited, as described above, only one conductance bridge 43 would result.

In a manner known per se, a conductance sensor 25 generates—based on the electrical current flowing between particular electrode 31 and crop-material flow 5—an ohmic resistance, which is ultimately converted in signal-processing device 26 assigned directly to conductance sensor 25 into a frequency f in Hz, which corresponds to conductance LW that is determined. Conductance value(s) LW is/are then transmitted to evaluation unit 38, in which a first check routine 41 runs a plausibility check—depending on crop material parameters, machine parameters, and sensor parameters to be described in greater detail—as to which of the determined conductance values LW are taken into account, and, therefore, which conductance measurement bridge 43a-c should generate the data for determining the conductance as the measurement method progresses. If, due to the short circuit of two electrodes 31, only one conductance bridge 43 exists, its conductance value LW is used directly as the basis in the further data-generation process.

In a next step, selected conductance value LW is used to calculate—together with temperature 41 of crop-material flow 5 generated by temperature sensor 42a, b, and/or temperature 41 of its environment—a temperature-compensated moisture content 40. Moisture content 50 determined is described by the equation $$F = a_0 \cdot f + a_1 \cdot T + a_2 \cdot P_i + \ldots + a_n$$

in which F is inventive moisture content 40, frequency f is conductance LW, T is crop-material and/or ambient temperature 41 determined by temperature sensor 42a, b, P are further crop-material and/or machine-specific parameters 47 that may have been accounted for, and $a_0$ through $a_n$ are special coefficients. The coefficients $a_0$ through $a_n$ result from a special calibration method, in which a reference moisture of crop-material flow 5 passing through agricultural machine 1 is determined under laboratory conditions, and the reference humidity is ultimately graphed in relation to conductance LW that was determined and represented as frequency f, and in relation to crop-material and/or ambient temperature 41 that was determined using temperature sensor 42a, b. Moisture content 40, crop-material and/or ambient temperature 41, and the reference moisture that were determined are then plotted in a three-dimensional X-Y-Z coordinate system 45.

The family of points plotted in the coordinate system defines a results area 46. Based on results area 46, coefficients $a_0$, $a_1$, $a_n$ are then derived, such that coefficient $a_0$ represents the slope of a region of results area 46 in the direction of the x-axis, coefficient $a_n$ represents the slope of a region of results area 46 in the direction of the y-axis, and coefficient $a_n$ represents the intersection of results area 46 with the z-axis of three-dimensional coordinate system 45.

Moisture content 40 determined in this manner is then transmitted via a further signal and data-transmission device 27 to display unit 39, where it is displayed to the operator of agricultural machine 1. As described above, display unit 39 and evaluation unit 38 may also be combined to form one single evaluation and display unit 29. In addition, a very precise value for moisture content 40 that optimally reflects the actual conditions is therefore available, which may be used, e.g., to determine a highly precise value for the crop-material throughput passing through agricultural machine 1. It is within the framework of the present invention to determine and visualize—instead of moisture content, which represents the component "water content"—the component "content of dry mass" directly.

A further qualitative improvement of crop-material moisture 40 to be determined is attained by taking into account the at least one further crop-material specific and/or machine-specific parameter P, 47 in the determination of moisture content 40. The at least one further crop-material specific and/or machine-specific parameter 47 is crop-material throughput 48 and/or layer thickness 49 of crop-material flow 5 detected by inventive conductance sensor 25 and/or crop-material type 50 and/or density 51 of crop-material flow 5 in the region of the conductance sensor 25 and/or pressing force 52 of crop-material flow 5 in the region of conductance sensor 25. Parameters 47 that have been provided are of great significance because investigations have shown that conductance LW generated by conductance sensor 25 described is influenced mainly by crop-material throughput 48 moving past conductance sensor 25 at any moment, and by its layer thickness 49 and material density 51.

This is due, in particular, to the fact that all three parameters 48, 49, 51 mainly define the conductivity of crop-material flow 5 to be detected. Since the cellular structure of the plants that constitute crop-material flow 5 also influences the conductivity of crop-material flow 5, and this cellular structure fluctuates greatly from plant type to plant type, it is advantageous to also account for the type of crop material 50 in the determination of the conductance. Since conductance sensor 25 generates conductance LW via more or less intensive contact of its electrodes 31 with crop-material flow 5 to be detected, the intensity of the contact between crop-material flow 5 and electrodes 31 of conductance sensor 25 is also of great significance. The conductivity of a substance that is detected decreases as the contact with a conductance sensor 25 decreases. Pressing force 52 that crop-material flow 5 exerts on electrodes 31 of conductance sensor 25 is therefore also taken into account, since pressing force 52 is ultimately synonymous with the intensity of the contact between crop-material flow 5 to be detected and conductance sensor 25.

In the simplest case, different characteristic curves 53 may be stored for various crop-material types 48 in evaluation unit 38 in order to determine moisture content 40. In this case, the operator of agricultural machine 1 enters—via a user interface 54 assigned to evaluation and/or display unit 38, 39—related crop-material type 50, and evaluation unit 38 automatically accesses characteristic curves 53 stored for this crop-material type 50. In an analogous manner, a large number of characteristic curves 53 may also be stored for each of the parameters 47 mentioned above, so that characteristic curves 53 that offer the best description for the specific application may be used to determine moisture content 40. It is also within the scope of the present invention for stored characteristic curves 53 to account for a combination of several of the parameters 47 described above.

If agricultural working machine 1 is designed as forage harvester 2, the crop-material specific parameter pressing force 52—per FIG. 2—may be determined in the region of conductance sensor 25 based on ejection speed $v_G$ of crop-material flow 5 in the region of conductance sensor 25, the width of passage 17 (FIG. 1) of a post-accelerator 12 located upstream of inventive measuring device 23, and/or impact point 55 (FIG. 2) of crop-material flow 5 in the region of conductance sensor 25.

In an even more compact version, inventive measuring device 23 may be designed such that evaluation unit 38 is also integrated directly in dust cover 24, which encloses conductance sensor 25. In this case, signal and data-transmission device 27 that is (assigned to?) conductance sensor 25 and extends out of dust cover 24 directly transmits determined crop-material moisture content 40 or the corresponding value for the content of dry substance to display device 39 or a bus system 56, which is known per se and is therefore not described in greater detail, and which is assigned to agricultural machine 1, so that the data that are determined are also available for use in other operations, e.g., to determine throughput.

It will be understood that each of the elements described above, or two or more together, may also find a useful application in other types of constructions differing from the types described above.

While the invention has been illustrated and described as embodied in a agricultural working machine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. An agricultural working machine for harvesting crop material embodying a forage harvester and including a measuring device for measuring a moisture content of a crop material flow passing through the agricultural working machine during harvesting operation, the measuring device comprising:
   at least one conductance sensor, said at least one conductance sensor comprising at least two electrodes arranged on a base plate and configured for determining the moisture content, and
   only one temperature sensor provided for temperature compensation and integrated in said conductance sensor,
   wherein the only one temperature sensor is arranged on the base plate with the at least two electrodes, and the base-plate is installed on the agricultural working machine,
   wherein the moisture content is determined at the conductance sensor via a temperature-compensated detection of conductance of the crop material flow contacting the at least two electrodes; and
   wherein the conductance sensor is positioned in a region of impact of the crop-material flow accelerated by a post-accelerator, wherein the region of impact is located on a top wall of an inside of an upper discharge chute of the forage harvester that ejects the crop-material.

2. The agricultural working machine as defined in claim 1, wherein said at least one conductance sensor is configured so that as the moisture content is determined, at least one further parameter selected from the group consisting of a crop-material specific parameter, a machine-specific parameter, and both is taken into account.

3. The agricultural working machine as defined in claim 2, wherein said at least one conductance sensor is configured so that said at least one parameter is a parameter selected from the group consisting of a crop-material throughput, a layer thickness of the crop-material flow detected by the conductance sensor, a crop-material type, a density of the crop material flow in a region of the conductance sensor, a pressing force of the crop material flow in a region of the conductance sensor, and combinations of thereof.

4. The agricultural working machine as defined in claim 3, wherein the agricultural working machine is a forage harvester, said conductance sensor is configured so that the crop-material specific parameter pressing force of the crop material flow in the region of the conductance sensor is determined based on an ejection speed of the crop material flow in the region of the conductance sensor, a width of the passage of a post-accelerator located upstream of the conductance sensor and/or an impact point of the crop-material flow in the region of the conductance sensor.

5. The agricultural working machine as defined in claim 1, wherein said at least one conductance sensor includes three electrodes positioned in a triangular configuration.

6. The agricultural working machine as defined in claim 5, wherein said triangular configuration of said electrodes of said conductance sensor is oriented such that it points in a direction selected from the group consisting of in a direction of the crop material flow and in a direction against the crop a-material flow.

7. The agricultural working machine as defined in claim 5, wherein the only one temperature sensor is assigned to at least one of the electrodes of the conductance sensor.

8. The agricultural working machine as defined in claim 1, wherein said conductance sensor has electrodes which are coupled with each other such that a conductance measurement bridge is formed between two of said electrodes, and further comprising an evaluation unit carrying out a comparison of detected conductance value and a selection of a conductance value.

9. The agricultural working machine as defined in claim 1, wherein said conductance sensor includes at least two electrodes which are short-circuited, so that only one conductance measurement bridge results between said electrodes, and further comprising an evaluation unit to which a determined conductance value is transmitted.

10. The agricultural working machine as defined in claim 1, wherein said conductance sensor has electrodes which are vertically positioned in said conductance sensor and their vertical positioning is adjustable.

11. The agricultural working machine as defined in claim 1, wherein said conductance sensor has electrodes which are integrated in a base plate, and said base plate is integrated in the agricultural working machine in two positions that are offset by 180°.

12. The agricultural working machine as defined in claim 1, wherein said conductance sensor includes electrodes which are enclosed in enclosures composed of wear-resistant material.

13. The agricultural working machine as defined in claim 12, wherein said enclosures are configured to be aerodynamic in a direction of material flow.

14. The agricultural working machine as defined in claim 1, wherein said conductance sensor includes a housing that is configured as a dust cover, and further comprising a signal-processing device provided in said conductance sensor and an evaluation unit assigned to the agricultural working machine and both integrated in said housing configured as said dust cover.

15. The agricultural working machine as defined in claim 1, and further comprising a display unit in which the determined moisture content or its equivalent and/or a content of dry mass, is depicted, and a evaluation unit in which these parameters are stored such that they are recallable.

* * * * *